United States Patent [19]

Kadaba

[11] Patent Number: 6,083,964
[45] Date of Patent: Jul. 4, 2000

[54] OPTICAL RESOLUTION OF RACEMIC AMINOALKYLPYRIDINE ANTICONVULSANTS AND (+) AMINOALKYLPYRIDINE ENANTIOMERS AS HIGHLY POTENT ORALLY EFFECTIVE ANTICONVULSANT DRUGS AND EXCITATORY AMINO ACID ANTAGONISTS

[75] Inventor: Pankaja K. Kadaba, Chadds Ford, Pa.

[73] Assignee: K and K Biosciences, Inc., Chadds Ford, Pa.

[21] Appl. No.: 09/251,353

[22] Filed: Feb. 17, 1999

Related U.S. Application Data

[60] Provisional application No. 60/075,108, Feb. 18, 1998.
[51] Int. Cl.[7] .......................... A61K 31/44; C07D 211/70
[52] U.S. Cl. ................................. 514/357; 546/329
[58] Field of Search .............................. 546/329; 514/357

[56] References Cited

U.S. PATENT DOCUMENTS

| | | | |
|---|---|---|---|
| 4,511,572 | 4/1985 | Kadaba | 514/340 |
| 4,610,994 | 9/1986 | Kadaba | 514/340 |
| 4,618,681 | 10/1986 | Kadaba | 546/276 |
| 4,689,334 | 8/1987 | Kadaba | 514/340 |
| 4,820,721 | 4/1989 | Kadaba | 514/359 |
| 5,206,254 | 4/1993 | Gandolfi et al. | 544/369 |
| 5,648,369 | 7/1997 | Kadaba et al. | 546/334 |

OTHER PUBLICATIONS

Williams et al.—Importance of Drug Enantiomers in Clinical Pharmacology—Drgs 30: 333–354 (1985).
Kadaba, et al.—Triazolines—XXVII.$\Delta^2$–1,2,3–Triazoline Anticonvulsants: Novel 'Built–in' Heterocyclic Prodrugs with a Unique 'Dual–Action' Mechanism for Imparing Excitatory Amino Acid L–Glutamate Neurotransmission[1], Bioorganic & Medicinal Chemistry, vol. 4, No.2, pp 165–178, 1996.
James McNamara et al.—The Kindling Model of Epilepsy: A Review, Progress in Neurobiology, vol. 15, pp 139 to 159 (1980).
John Caldwell et al.—The pharmacological and toxicological significance of the sterochemistry of drug disposition, Xenobiotica, 1988, vol. 18, Supp. No. 1, 59–70.
Deshmukh et atl.—Identification of the Triazoline Pharmacophore and the Evolution of the Aminoalkylpyridines. A new class of Potent Orally Active Anticonvulsant Agents, Medicinal Chemistry Research, 1993, vol. 3 pp. 223–232.
Ariens—Nonchiral, homochiral and composite chiral drugs—1993, Elsevier Science Publishers, Ltd.
Simonyi—On Chiral Drug Action—The Central Research Institute for Chemistry, Hungarian Academy of Sciences, pp 359–413 (1993).
Porter—Mechanisms of Action of New Antiepileptic Drugs, Epilepsia 30(Suppl 1):S29–S34, 1989.
Foster, et al.—Acidic Amino Acid Binding Sites in Mammalian Neuronal Membranes: Their characteristics and Relationship to Synaptic Receptors, Brain Researh Reviews, 7 (1984) 103–164.
Watkins—Excitatory Amino Acid Transmitter—Ann. Rev. Pharmacol. Toxicol, 1981, 21:165–204.
Racine—Kindling: The First Decade—Neurosurgery, vol. 3, No. 2, 1978, pp. 234–252.
Schwarcz, et al.–Excitatory Amino Acids and Epilepsy, Plenum Press, New York, 1986.
Watkins et al.—Excitatory Amino Acid Transmitters, Annual Reviews in Pharmacology & Toxicology, 1982, vol. 21, pp 165–204.
Porter et al.—Antiepileptic Drug Development Program, Cleveland Clinic Quarterly, vol. 51, No. 2, 1984, pp. 293–305.
Porter et al.—Antiepileptic Drugs—In Basic and Clinical Pharmacology 4th Edn., pp. 287–303.
Stinson—Chiral Drug Market Shows Signs of Maturity, Chemical and Engineering News, Oct. 20, 1997, pp. 38–70.
Stinson—Chiral Drugs, Chemical & Engineering News, Sep. 27, pp. 38–65–1993.
Stinson—Counting on Chiral Drugs, Chemical and Engineering News, Sep. 21, 1998, pp. 83–104.

*Primary Examiner*—Zinna Northington Davis
*Assistant Examiner*—Binta Robinson
*Attorney, Agent, or Firm*—McDermott, Will & Emery

[57] ABSTRACT

A specific method of optical resolution using dibenzoyltartrate (DBTA) is described for the preparation of six new (+) and (−) enantiomers each of six racemic aminoalkylpyridines. The (+) enantiomers are potent orally active, non-neurotoxic anticonvulsant compounds that are highly effective in the MES test and the hippocampal kindled rat model with no activity in the sc Met test and that significantly raise seizure threshold in the i.v. Metrazol seizure threshold screen. Pharmaceutical compositions, to treat convulsive disorders, comprising as the active ingredient one of the above (+) or (−) aminoalkylpyridine enantiomers, that are selected from the groups of enantiomers consisting of those of the formulae:

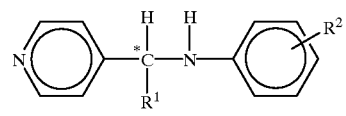

(+) AAP Enantiomers

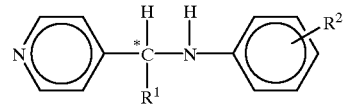

(−) AAP Enantiomers wherein $R^1$ is methyl or ethyl and $R^2$ is 3,4-dichloro, p- or m-chloro or p-bromo. The compositions are administered to mammals in an amount to provide a dosage amount ranging from about 10 mg/kg to 200 mg/kg of body weight.

35 Claims, No Drawings

OPTICAL RESOLUTION OF RACEMIC AMINOALKYLPYRIDINE ANTICONVULSANTS AND (+) AMINOALKYLPYRIDINE ENANTIOMERS AS HIGHLY POTENT ORALLY EFFECTIVE ANTICONVULSANT DRUGS AND EXCITATORY AMINO ACID ANTAGONISTS

RELATED APPLICATIONS

This application claims priority from U.S. Provisional Application No. 60/075,108, filed Feb. 18, 1998, which is incorporated herein by reference.

FIELD OF THE INVENTION

This invention relates to novel anticonvulsant aminoalkylpyridine (AAP) optical stereoisomers of enantiomers and their specific method of preparation. More particularly it relates to novel (+) AAP enantiomers that are more selective in their anticonvulsant action than the respective racemic AAPs which comprise a mixture of both the (+) and the (−) AAP enantiomers, and are useful as excitatory amino acid inhibitors and as highly potent orally effective antiepileptic pharmaceutical compositions with no neurotoxicity.

BACKGROUND ART

Epilepsy is a leading neurological disorder. One to four million Americans and twenty to forty million people worldwide suffer from some form of epilepsy, making it second only to stroke as the leading neurological disorder. Although standard therapy permits control of seizures in 80% of these patients, one-half million people in the U.S. have uncontrolled epilepsy. The number of drugs useful for the treatment of epilepsy is remarkably small. Fewer than 20 drugs are currently marketed in the U.S., and of these, only five or six are widely used. Complex partial epilepsy (also known as temporal lobe, psychomotor or limbic epilepsy), the most devastating form among adults, and estimated to account for as many as two-thirds of all cases, is refractory to drug treatment [Gummit, R. J., "The Epilepsy Handbook, The Practical Management of Seizures", Raven Press, New York, 1983]. It is becoming increasingly evident that significant progress toward complete control can be achieved only by an understanding of the mechanisms of the epilepsies themselves, which will provide the molecular basis for antiepileptic drug design and development, and new treatment strategies.

NMDA (N-methyl-D-aspartate) receptor overstimulation by high levels of the excitatory amino acid (EAA), L-glutamate, has been implicated in epileptogenesis and epilepsy [Cavalheiro, et al., "Frontiers in Excitatory Amino Acid Research", A. R. Liss, New York, 1988]. Thus, development of agents that are EAA/NMDA antagonists may constitute novel and effective therapies for the epilepsies. Although a number of EAA inhibitors has been discovered, many lack NMDA receptor specificity and are too toxic for clinical studies [Porter, *Epilepsia*, 30 S29–34, 1989].

Thus, the successful optical resolution of several racemic AAPs and the discovery of this invention of the (+) enantiomers of the AAPs as a superior, more potent class of anticonvulsant agents in the Applicant's laboratories are significant. The (+) AAP enantiomers of this invention, derived from the optical resolution of the corresponding racemic mixtures of anticonvulsant AAP compounds (Kadaba, P. K, U.S. Pat. No. 5,648,369, Jul. 15, 1997), are highly potent, orally effective, 20 nonneurotoxic EAA antagonists with very high therapeutic or protective index values ($TD_{50}/ED_{50}$, the ratio of toxic dose in 50% of the animals to the effective dose in 50% of the animals) better than that of the racemic AAPs, and hold promise for commercial development as nontoxic, clinically useful antiepileptic drugs for the management of epilepsy in humans.

SUMMARY OF THE INVENTION

It is accordingly one object of the present invention to provide several new and novel (+) AAP enantiomers and their specific methods of preparation by appropriately modified methods of optical resolution of the racemic AAP compounds.

It is a further object of the present invention to provide anticonvulsant agents which comprise (+) AAP enantiomers derived from specific methods of optical resolution of racemic AAPs.

A further object of the present invention is to provide a method for the treatment of convulsive disorders by administration of an effective amount of the (+) AAP enantiomers of this invention.

A further object of the present invention is to provide (+) AAP enantiomers belonging to different structural classes and methods for their use in the treatment of neurological disorders such as epilepsy and stroke.

A still further object of the present invention is to provide (+) AAP enantiomers as inhibitors of the EAA neurotransmitter L-glutamate. The (+) AAP enantiomers of this invention, afford pronounced protection in the maximal electroshock seizure (MES) model in both mice and rats, by the intraperitoneal and oral route, respectively, which is indicative of their action as glutamate antagonists. Furthermore, they afford protection in the kindling model of epilepsy, which provides additional support for their action as glutamate antagonists.

A still further object of the present invention is to provide anticonvulsant compositions which are highly active by the oral route and which contain as the essential ingredient certain (+) AAP enantiomers and use of these (+) AAP enantiomers as highly potent orally active, nonneurotoxic antiepileptic drugs in the treatment of convulsive disorders such as epilepsy.

Other objects and advantages of the present invention include use of the (+) AAP enantiomers, obtained by specific methods of optical resolution of the respective racemic AAPs, in the treatment of stroke and other neurological disorders such as Parkinson's disease, where too excessive glutamate exists, by virtue of their action as EAA antagonists and inhibitors of L-glutamate neurotransmission.

In satisfaction of the foregoing objects and advantages, there are provided by this invention several (+) AAP enantiomers derived from specific methods of optical resolution of racemic AAPs, which are useful as anticonvulsant drugs. The various classes of (+) AAP enantiomers may be characterized by the following general formulae:

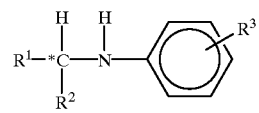

(+) AAP Enantiomers (*C, asymmetric carbon atom)

wherein $R^1$ is 3-pyridyl, or 4-pyridyl, $R^2$ is methyl or ethyl and $R^3$ is 3, 4-dichloro, p- or m-chloro, p- or m-bromo, p- or m-fluoro, p- or m-trifluoromethyl, p-lower alkyl, p-lower alkoxy or hydrogen.

Also provided by this invention are highly orally active, nontoxic anticonvulsant compositions comprising as the active ingredient, a compound selected from those of the following formulae:

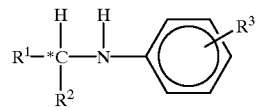

(+) AAP Enantiomers (*C, asymmetric carbon atom)

wherein $R^1$ is 3-pyridyl or 4-pyridyl, $R^2$ is methyl or ethyl, and $R^3$ is 3,4-dichloro, p- or m-chloro, p- or m-bromo, p- or m-fluoro, p- or m-trifluoromethyl, p- lower alkyl, p-lower alkoxy or hydrogen.

Also provided are methods for the administration of the anticonvulsant compositions of this invention to mammals including animals and humans in the treatment of convulsive disorders such as epilepsy including complex partial seizures.

DESCRIPTION OF PREFERRED EMBODIMENTS

As indicated above, this invention relates to several new compounds belonging to several different substituted (+) AAP enantiomers which are useful as antiepileptic agents. In one group of (+) AAP enantiomers, the $R^1$ is 3-pyridyl and in the second group, $R^1$ is 4-pyridyl. In both groups of (+) AAP enantiomers of this invention, the $R^2$ group on the carbon bearing the pyridyl ring is methyl or ethyl. The (+) AAP enantiomers of this invention are further substituted on the N-phenyl group by $R^3$, and $R^3$ is 3,4-dichloro, p-chloro, or m-chloro, p- or m-bromo, p- or m-fluoro, p- or m-trifluoromethyl, p-lower alkyl, p-lower alkoxy or hydrogen. The (+) AAP enantiomers of this invention have highly potent oral anticonvulsant activity without neurotoxicity as antiepileptic drugs in the treatment of convulsive disorders such as epilepsy including complex partial seizures.

In one aspect of the present invention, two groups each of (+) AAP enantiomers are provided which have potent oral antiepileptic activity and which are of the following general formulae:

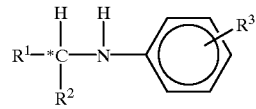

(+) AAP Enantiomers (*C, asymmetric carbon atom)

In the above formulae, $R^1$ is 4-pyridyl, and $R^2$ is methyl or ethyl and leads to the two groups of (+) AAP enantiomers. When $R^1$ is 4-pyridyl, $R^2$ can be methyl or ethyl and $R^3$ can be 3,4-dichloro, p-chloro, or m-chloro or p-bromo. Those compounds wherein $R^1$ is 4-pyridyl, $R^2$ is methyl or ethyl and $R^3$ is 3,4-dichloro, p-chloro, m-chloro or p-bromo, are new and novel compounds.

In a second aspect of this invention, there are provided novel anticonvulsant compositions which are highly orally active and nontoxic, and which comprise as the active ingredient an effective amount of a compound selected from those of the following formulae:

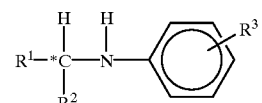

(+) AAP Enantiomers (*C, asymmetric carbon atom)

wherein $R^1$ is 4-pyridyl, $R^2$ is methyl or ethyl and $R^3$ is 3,4-dichloro, p-chloro, m-chloro, or p-bromo.

There are further provided by this invention methods for administration of the anticonvulsant composition to mammals including animals and humans.

In a third aspect of this invention, there are provided (+) AAP enantiomer compounds of the formulae:

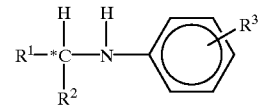

(+) AAP Enantiomers (*C, asymmetric carbon atom)

wherein $R^1$ is 4-pyridyl, $R^2$ is methyl or ethyl, $R^3$ is 3,4dichloro, p-chloro, m-chloro, or p-bromo, and which exhibit pronounced and selective activity in the MES test Significance of Pronounced, Selective Activity in the MES Test The (+) AAP enantiomers prepared by specific methods of optical resolution of racemic AAPs in this invention exhibit pronounced and highly selective anticonvulsant activity in the maximal electroshock seizure (MES) test but show no activity in the subcutaneous Metrazole test (scMet). The selective activity of the compounds of this invention in the MES test is of great significance, because partial seizures in humans correlate positively with experimental seizures elicited by the MES test [Porter, R. J. and Pitlick, W. H., In "Basic and Clinical Pharmacology", 4th Edn., B. G. Katzung Ed., Appleton & Lange, C.A., 1989, pp 287–303]. Since antiepileptic drugs effective against MES seizures alter ionic transport across excitable membranes, the (+) AAP enantiomers obtained by optical resolution of racemic AAPs that evince significant activity in the MES test, may be expected to attenuate EAA neurotransmission. Since there is strong evidence that the excitatory neurotransmitter L-glutamate plays a key role in EAA neurotransmission along limbic circuits which are particularly relevant to kindling epileptogenesis [McNamara, J. O., Bryne, M. C., Dasheiff, R. M., and Fitz, J. G., *Prog. Neurobiol.*, 15, 139–159 (1980)], the (+) AAP enantiomers of this invention could be expected to be effective glutamate antagonists and afford protection in human complex partial (limbic) epilepsy.

Significance of the Protection Afforded by the (+) AAP Enantiomers in the Kindling Model of Epilepsy The kindling animal model of epilepsy is accepted as a model of human complex partial (limbic) epilepsy. The kindling phenomenon mimics human epilepsy and there is increasing evidence that EAAs play an important role in kindling.

Both the (+) and (−) enantiomers of N-(4-chlorophenyl)-1-(4-pyridyl)ethylamine afford protection in the hippocampal kindled rats, by the i.p. route. While the (−) enantiomer protects only two out of eight (2/8) animals at 100 mg/kg, the (+) enantiomer protects six out of seven (6/7) at the same dose and has an $ED_{50}$ of 54.92 mg/kg, at which the seizure score and afterdischarge duration are significantly reduced from that of the control. The significant protection afforded by the (+) N-(4-chlorophenyl)-1-(4-pyridyl)ethylamine is indicative of the therapeutic usefulness of this compound in the control of complex partial seizures, which at present is refractory to drug treatment.

"Kindling" refers to the process whereby repeated administration of an initially subconvulsive electrical stimulus results in progressive intensification of epileptic discharge culminating in a generalized seizure. Kindling can be induced by electrical stimulation of many sites in the brain, especially in "limbic" areas, which include amygdala, hippocampus, and entorhinal cortex [Racine, R., Neurosurgery, 3, 234–252 (1978)]. Kindling is reliably produced by a one second train of 60 Hz square wave stimuli of one millisecond duration at current levels which initially produce only a slight afterdischarge (AD), but no behavioral response. Repeated stimulation, typically once daily, results in a progressive increase in AD amplitude, duration and complexity with subsequent spread to other brain areas culminating in a fully generalized motor seizure. [Racine, R. J. and Zaide, J., In "Mechanisms, the Continuing Evolution of the Limbic System Concept" (K. E. Livingston and O. Hornykiewicz, eds.), Plenum Press, pp. 457–493, 1978.

The development of kindling in the rat has been characterized by five (1 to 5) behavioral and electrographic "classes". The behavior in classes 1 (facial clonus) and 2 (head nodding) mimics that found in human complex partial seizures; the behavior in other classes would be consistent with limbic seizures evolving to generalized motor seizures. An animal is considered to be fully kindled once the enhanced sensitivity has developed, as evidenced by a class 5 seizure (rearing and falling).

Aminoalkylpyridines as Racemic (±) Mixtures Versus (+) AAP or (−) AAP Enantiomers Studies by the Applicant on the metabolism and pharmacology of triazoline anticonvulsants, led to the evolution and discovery of the aminoalkylpyridines (AAPs) as a unique class of orally active anticonvulsant agents, superior to the triazolines themselves [Kadaba, P. K., et al., Bioorg. Med. Chem., 2, 165–178 (1996); Kadaba, P. K, U.S. Pat. Nos. 4,511,572, 1985; 4,618,681, 1986; 4,689,334, 1987; 4,610, 994, 1986; 4,820,721, 1989]. Work on the AAPs indicate that they are as a class, nontoxic, and effective by the oral route, with protective indices greater than 20. The AAPs also show high anticonvulsant activity in the MES test and are practically inactive in the scMet test (Deshmukh, T. R. & Kadaba, P. K, Med. Chem. Res., 3 223–232, 1993; Kadaba, P. K., U.S. Pat. No. 5,648,369 (1997)].

The AAPs are racemic compounds and comprise of a mixture of (+) and (−) enantiomers or optical isomers. The carbon atom bearing the pyridyl and the alkyl group in the AAPs (the *C in the structures), has four different groups attached to it and is referred to as an asymmetric carbon and provides a chiral center in the molecule. The racemic AAPs comprise of a mixture of two optical isomers, the (+) enantiomer and the (−) enantiomer. The two enantiomers turn the plane of polarization of polarized light in opposite directions, but to the same degree or extent. Enantiomeric separation by optical resolution and identification as to which one of the two enantiomers is responsible for the pharmacological (anticonvulsant) activity of the AAPs, would aid in increasing the drug potency and the drug specificity and further enhance the commercial potential of these antiepileptic agents.

The biological significance of enantioselective metabolism and the importance of stereochemistry in pharmacology and toxicology are being recognized more and more in recent years (Caldwell et al., Xenobiotica, 18, 59–70, 1988, Williams & Lee, Drugs, 30, 333–354, 1985; Simonyi, Med. Res. Revs., 4, 359–413, 1984) and of late many enantiomeric drugs with improved pharmacological activity over the racemates are beginning to make it into the market (Stinson, Chem. Eng. News, September 27, pp. 38–65, 1993). The pharmacokinetic and pharmacodynamic differences between the enantiomers are important and a nonstereoselective approach to the study of chiral drugs is often inaccurate and misleading. The enantiomeric AAPs may reduce the long-term hazards associated with drugs that are taken for long periods in one's lifetime, such as in epilepsy, and thus they have great potential for commercial development. Thus, in the present invention, several of the (+) AAP enantiomers show far greater potency in the MES test and much higher protective index (P.I.) values than the parent racemic AAPs, as well as the (−) AAP enantiomers.

NMDA receptor overstimulation by glutamate is implicated in epileptogenesis and epilepsy. Thus, NMDA antagonists also provide prophylaxis and seizure protection. There is a definite need for safer, orally active NMDA antagonists, to afford effective therapies for the epilepsies. Excessive levels of glutamate are suspected not only in epilepsy, but in several other neurological disorders, eg. stroke. Thus, the nontoxic, orally active NMDA antagonists developed from the (+) AAP enantiomers of this invention, have good potential for commercial application as clinically useful antiepileptic drugs and also as neuroprotective agents in related neurological disorders such as stroke, Parkinson's disease, etc.

This invention relates to novel, new and previously unknown (+) AAP enantiomers derived by specific methods of optical resolution of the racemic AAPs, as a unique class of potential EAA antagonists, effective in the MES test and the hippocampal kindled rat model, their methods of preparation, and compositions for their use as a novel class of antiepileptic drugs in the treatment of convulsive disorders such as epilepsy including partial seizures.

Considerable evidence has accrued in the last decade and a half implicating amino acids in chemical neurotransmission; while GABA (gamma-aminobutyric acid) and glycine serve as inhibitory neurotransmitters, L-glutamate and L-aspartate function as excitatory neurotransmitters in the central nervous system [Foster, A. C. and Fagg, G. E., Brain Res. Rev., 7, 103 (1984)]. There exist considerable data that suggest excitatory amino acids (EAAs) may be critically involved in both epileptogenesis and as a focus for the mechanism of action of anticonvulsants (Meldrum, B. S., and Chapman, A. G., In "Glutamine, Glutamate, and GABA in the Central Nervous System," L. Hertz, et al., Ed.,Alan R. Liss, Inc., New York 1983, pp. 625–641; R. Schwarcz and Yehezkel-Ben Ari, Eds., "Excitatory Amino Acids and Epilepsy", Plenum Press, New York, 1986). Because brain function in the normal state is a dynamic balance of excitatory and inhibitory processes, one would think that excessive neuronal activity leading to seizures may result from either an increase in excitatory transmission, or alternately, from a decrease in inhibitory transmission. Thus, effecting changes in the concentrations of either excitatory or inhibitory neurotransmitters at their synapses would represent potential mechanisms of anticonvulsant action and strategies for anticonvulsant drug design.

Strong evidence exists for the prominent role of EAAs in excitatory transmission along limbic circuits which are believed to be particularly relevant to kindling epileptogenesis. More recently, evidence for a causal connection between EAA release and onset of hyperactivity has been provided by the use of specific EAA receptor antagonists in various models of epilepsy [Watkins, J. C., and Evans, R. H. Ann. Rev. Pharmacol. Toxicol., 21, 165 (1982)]. There is mounting evidence that the excitatory neurotransmitters, L-glutamate and L-aspartate, play a key role in the spread of epileptic activity from one brain region to another and may also be contributing to its initiation (Meldrum, B. S., In "Handbook of Experimental Pharmacology: Antiepileptic Drugs," H. H. Frey and D. Janz Ed., Berlin, 1984). EAA agonists are convulsants and EAA antagonists show anticonvulsant activity in a variety of seizure models. NMDA receptor overstimulation by high levels of L-glutamate has been implicated in epileptogenesis and epilepsy. NMDA receptor antagonists that block the action of L-glutamate, and thus the overstimulation of the NMDA receptor, may represent novel antiepileptic agents that can afford both prophylaxis as well as seizure protection.

The compounds of the present invention are useful in pharmaceutical compositions using conventional pharmaceutical carriers or vehicles for administration to humans and animals in unit dosage forms, such as tablets, capsules, pills, powders, granules, suppositories, sterile parenteral solutions or suspensions, sterile non-parenteral solutions or suspensions, oral solutions or suspensions, oil in water or water in oil emulsions and the like, containing suitable quantities of the active ingredient.

The (+) AAP enantiomers of this invention along with the (−) AAP enantiomers may be prepared by the optical resolution of racemic AAPs by specifically using (+) dibenzoyltartaric acid (DBTA) or (−) DBTA. Other resolving agents were not found to be suitable for the successful resolution of racemic AAPs. By using DBTA, enantiomers with good optical purity were obtained in good yields. The AAPs are treated with the appropriate DBTA agent and the resulting diastereomeric salts are subjected to acid hydrolysis to yield the free (+) or (−) enantiomers wherein $R^1$ is 4-pyridyl and $R^2$ is methyl or ethyl when $R^3$ is 3,4-dichloro, p-chloro, m-chloro or p-bromo as shown in Equation 1.

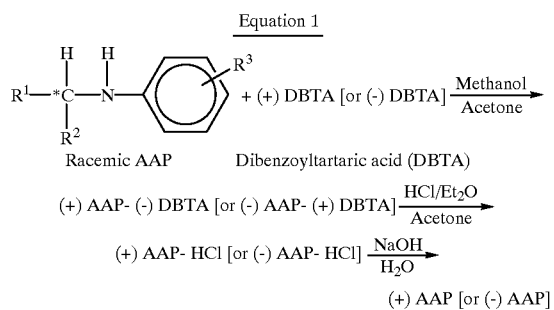

Racemic AAP     Dibenzoyltartaric acid (DBTA)

(+) AAP- (−) DBTA [or (−) AAP- (+) DBTA] $\xrightarrow{\text{HCl/Et}_2\text{O}}{\text{Acetone}}$ (+) AAP- HCl [or (−) AAP- HCl] $\xrightarrow{\text{NaOH}}{\text{H}_2\text{O}}$ (+) AAP [or (−) AAP]

In the above equation, $R^1$, $R^2$ and $R^3$ are as defined above.

In the method of preparation, the racemic AAP compound is treated with the resolving agent, (+) or (−) dibenzoyltartaric acid (DBTA), and the diastereomeric salts are allowed to crystallize slowly at room temperature. The pure recrystallized salts are then treated with ethereal hydrogen chloride followed by generation of the free (+) and (−) enantiomers by neutralization with NaOH.

The following representative examples of enantiomer preparation are presented to illustrate the invention, but it is not to be considered as limited thereto. In the examples and throughout the specification, parts are by weight unless otherwise indicated.

EXAMPLE 1

Optical Resolution of Racemic N-(4-Chlorophenyl)-1-(4-pyridyl)ethylamine and Preparation of the (+) Enantiomer The resolving agent, (−) DBTA (0.2578 mole), and the racemic AAP compound (0.2578 mole) were each dissolved completely in acetone (100 ml), and the solutions were mixed in a beaker and allowed to stand at room temperature for 12 hours. The massive white precipitate was filtered by suction and washed with a mixture of acetone and petroleum ether (50 ml). The powdery material was air-dried for one day and recrystallized from a mixture of methanol (600 ml) and acetone (600 ml). After the salt was completely in solution, the mixture was concentrated to about 400 ml and cooled in the refrigerator for about 3 hours. The precipitate that was formed was suction filtered and washed with acetone petroleum ether mixture (2:1) and air-dried.

The above material was recrystallized again following exactly the same procedure until the optical rotation remained constant. The m.p. of the (+) AAP/(−) DBTA diastereomeric salt was 159–160° C., and the optical rotation, $[\alpha]^{23}$=−61.8 (C=0.94, CH$_3$OH).

The free (+) AAP enantiomer was generated in two steps. The finely powdered diastereomeric salt (0.11 mole) was suspended in acetone (300 ml) and ethereal hydrogen chloride (1M, 800 ml) was added to the suspension with vigorous stirring, when a lot of white precipitation appeared. The stirring was continued for 3 hours and then the mixture was cooled in the refrigerator for 3 hours. The massive white precipitation was suction filtered and immediately dissolved in water (1500 ml). To the resulting clear solution, a sodium hydroxide solution (20%, 300 ml) was added slowly, until the pH was equal to 8, when a cloudy solution was s obtained. It was allowed to stand in the hood for 24 hours and the white solid that precipitated out was suction filtered.

It was recrystallized from methyl tert-butyl ether (300 ml) and methanol (100 ml). The insoluble materials were filtered off, and the clear filtrate concentrated to a small volume (~50 ml), mixed with petroleum ether (~50 ml), and cooled for 2 hours. The white solid was filtered, washed with a mixture of methyl tert-butyl ether-petroleum ether, and air-dried. The product purity was determined by the optical rotation remaining constant. The (+) enantiomer was a crystalline white solid, yield, 73%, and m.p. 103–104° C.; retention time from chiral HPLC was 12.5 minutes, with an enantiomeric excess (e.e.) of 99.66%. The rotation was $[\alpha]^{23}$=+18.4 (C=1.67, ethanol).

Six examples of enantiomeric separations are reported in Table 1 along with their melting points and optical rotation. The general yields of the pure enantiomers were >65%.

All the AAP enantiomers presented in Table 1 were identified through their elemental analysis, melting points, optical rotation, $^1$H NMR and $^{13}$C NMR spectra.

The examples are presented to illustrate the invention, but it is not to be considered as limited thereto.

TABLE 1

| Compound | Melting Point, ° C. | Optical Rotation, $[\alpha]_D^{23}$ |
|---|---|---|
| (1) (+) N-(4-Chlorophenyl)-1-(4-pyridyl)ethylamine | 101–103 | +17.3° |
| (2) (−) N-(4-Chlorophenyl)-1-(4-pyridyl)ethylamine | 103–105 | −17.6° |
| (3) (+) N-(3-Chlorophenyl)-1-(4-pyridyl)ethylamine | 140–145 | +5.99 |
| (4) (−) N-(3-Chlorophenyl)-1-(4-pyridyl)ethylamine | 145–150 | −6.0 |
| (5) (+) N-(3,4-Dichlorophenyl)-1-(4-pyridyl)ethylamine | 133–135 | +20.5 |
| (6) (−) N-(3,4-Dichlorophenyl)-1-(4-pyridyl)ethylamine | 135–137 | −18.0 |

TABLE 1-continued

| Compound | Melting Point, °C. | Optical Rotation, $[\alpha]_D^{23}$ |
|---|---|---|
| (7) (+) N-(4-Chlorophenyl)-1-(4-pyridyl) propylamine | 90–115 | +47.4 |
| (8) (−) N-(4-Chlorophenyl)-1-(4-pyridyl) propylamine | 85–110 | −48.5 |
| (9) (+) N-(3,4-Dichlorophenyl)-1-(4-pyridyl) propylamine | 140–145 | +39.8 |
| (10) (−) N-(3,4-Dichlorophenyl)-1-(4-pyridyl) propylamine | 135–140 | −38.6 |
| (11) (+) N-(4-Bromophenyl)-1-(4-pyridyl) ethylamine | 101–104 | +26.1 |
| (12) (−) N-(4-Bromophenyl)-1-(4-pyridyl) ethylamine | 100–103 | −25.5 |

EXAMPLE 2

Optical Resolution of Racemic N-(4-Chlorophenyl)-1-(4-pyridyl)ethylamine and Preparation of the (−) Enantiomer The procedure used was essentially the same, except (+) DBTA was used as the resolving agent. The (−) enantiomer was obtained as white crystals, m.p. 102–104° C. with $[\alpha]^{23}=-17.5$ (C=1.0, ethanol).

EXAMPLE 3

The (+) AAP enantiomers obtained by optical resolution of racemic AAPs and the resulting highly orally effective anticonvulsant compositions of this invention are useful in the treatment of convulsive disorders. The oral potency of the compounds range from those which are very highly potent to those of very good medium potency, with no accompanying toxicity. A series of (+) AAP enantiomers and (−) AAP enantiomers of this invention has been evaluated for anticonvulsant activity by the intraperitoneal (i.p.) and by the oral (p.o.) route using two standard seizure models in the mouse and in the rat, the maximal electroshock seizure (MES) test and the subcutaneous pentylenetetrazol (Metrazole) seizure threshold (scMet) test. These two methods of seizure provocation reliably elicit well characterized seizure phenomena and together they have been shown sufficient to identity all compounds known to demonstrate anticonvulsant activity in other tests [Porter, R. J., et al., *Cleveland Clinic Quarterly*, 51, 293 (1984)]. While the (−) AAP enantiomers are more active than the racemic AAPs, the (+) AAP enantiomers are far superior in their potency and lack of toxicity.

Based on the screening results, the compounds are placed in one of three categories. Those failing to demonstrate anticonvulsant activity at doses up to 300 mg/kg are considered inactive. Class II compounds show anticonvulsant activity at doses greater than 100 mg/kg or show activity at 100 mg/kg which is not reinforced by similar activity at 300 mg/kg. Thus, compounds of class or group II demonstrate anticonvulsant activity without signs of neurological deficit, but do not have significant potency. The Class I compounds are those which are most promising as anticonvulsants. They demonstrate anticonvulsant activity in either the MES test or the scMet test, or both at doses of 100 mg/kg or 30 mg/kg without signs of neurological deficit and thus have an estimated protective index of greater than 1.

Neurotoxicity is determined by the rotorod ataxia test in mice and by the positional sense test and gait and stance test in the rat.

The following Table 2 presents the results of these anticonvulsant tests with respect to several (+) and (−) AAP enantiomeric compounds derived from optical resolution of racemic AAPs of the present invention. This Table 2 identifies the specific compounds tested by their chemical name and provides the test model, the route of administration, the animal species used, and the anticonvulsant activity and toxicity in terms of $ED_{50}$ and $TD_{50}$ values, (the median effective and toxic dose respectively), when intraperitoneally administered to mice, and when orally administered to rats.

TABLE 2

Comparison of Anticonvulsant Efficacy ($ED_{50}$ and $TD_{50}$, mg/kg) of AAP Enantiomers with Racemic AAPs in the MES Test.

| Compound | Mice, i.p. | | | Rat, p.o. | | | Rat, p.o. for racemic AAPs | | |
|---|---|---|---|---|---|---|---|---|---|
| | $ED_{50}$ | $TD_{50}$ | P.I. | $ED_{50}$ | $TD_{50}$ | P.I. | $ED_{50}$ | $TD_{50}$ | P.I. |
| (1) N-(4-Chlorophenyl)-1-(4-pyridyl)ethylamine | | | | | | | 22.9 [2.0] | >470.0 [0.0][a] | >20.5 |
| (+) Enantiomer | 35.9 [0.25][a] | 149.1 [0.25] | 4.2 | 10.2 [1.0] | >500.0 [0.0][a] | >49.1 | | | |
| (−) Enantiomer | 60.3 [2.0] | 219.4 [0.25] | 3.6 | 25.8 [6.0] | >500.0 [0.0][a] | >19.4 | | | |
| (2) N-(3-Chlorophenyl)-1-(4-pyridyl)ethylamine | | | | | | | 34.0 [0.25] | >500.0 [0.0][a] | >14.7 |
| (+) Enantiomer | 67% protection at 100 mg/kg[b] | | | 25–75% protection during 4 hour period[b] | | | | | |
| (−) Enantiomer | 33% protection at 100 mg/kg[b] | | | 50–100% protection during 4 hour period[b] | | | | | |
| | | | | 29.6 [1.0] | >62.5 [0.0][a] | >2.1 | | | |
| (3) N-(3,4-Dichlorophenyl)-1-(4-pyridyl)ethylamine | | | | | | | 29.7 [2.0] | >500.0 [0.0][a] | >16.8 |
| | 76.1 | >500.0 | >6.6 | 32.3 [2.0] | >500.0 [0.9][a] | >15.5 | | | |

TABLE 2-continued

Comparison of Anticonvulsant Efficacy (ED$_{50}$ and TD$_{50}$, mg/kg)
of AAP Enantiomers with Racemic AAPs in the MES Test.

| Compound | Mice, i.p. | | | Rat, p.o. | | | Rat, p.o. for racemic AAPs | | |
|---|---|---|---|---|---|---|---|---|---|
| | ED$_{50}$ | TD$_{50}$ | P.I. | ED$_{50}$ | TD$_{50}$ | P.I. | ED$_{50}$ | TD$_{50}$ | P.I. |
| (+) Enantiomer | [2.0] | [24.0] | | | | | | | |
| | | | | 0–100% protection during a 4-hour period[b] | | | | | |
| (−) Enantiomer | 125.4 [0.5] | 279.2 [24.0] | 2.2 | 25–75% protection during 4-hour period[b] | | | | | |
| (4) N-(4-Chlorophenyl)-1-(4-pyridyl)propylamine | | | | | | | 25.0 [2.0] | >500 [0.0][a] | >20 |
| (+) Enantiomer | 109.2 [2.0] | 321.7 [6.0] | 2.9 | 0–75% protection | | | | | |
| (−) Enantiomer | 118.9 [2.0] | 269.4 [0.25] | 2.3 | 25–100% protection during a 4-hour period | | | | | |
| (5) N-(3,4-Dichlorophenyl)-1-(4-pyridyl)propylamine | | | | | | | 0–50% protection during a 4-hour period | | |
| (+) Enantiomer | 91.9 [0.5] | 279.2 [24.0] | 3.0 | 0–75% protection during 4 hour period[b] | | | | | |
| (−) Enantiomer | 117.3 [2.0] | 275.2 [24.0] | 2.3 | 25–100% protection during 4 hour period[b] | | | | | |
| (6) N-(4-Bromophenyl)-1-(4-pyridyl)ethylamine | | | | | | | 20.9 [4.0] | >500.0 [1.0][a] | >23.9 |
| (+) Enantiomer | 34.7 [0.25] | 133.9 [0.25] | 3.9 | 9.3 [4.0] | >500.0 [0.0][a] | >53.7 | | | |
| (−) Enantiomer | 85.5 [2.0] | 287.6 [0.25] | 3.4 | 25–75% protection during 4-hour period[b] | | | | | |

[a]The time of peak effect at which test is done is given in [ ] below the ED$_{50}$ and TD$_{50}$ values. The time of test is given as 0.0 for TD$_{50}$, when no toxicity was observed over a 24-hour period for that dose.
[b]For those compounds where ED$_{50}$ and TD$_{50}$ values are not available, the percent protection afforded at 100 mg/kg by the i.p. route and at 30 mg/kg by the p.o. route is given. Observation is made in rat, p.o. at 5 time points, 0.25, 0.5, 1, 2, and 4 hours using 4 rats for each point and only the lowest and highest % protection are shown.

As shown in Table 2, all the (+) AAP enantiomers demonstrate consistently superior anticonvulsant activity without signs of neurological deficit as compared to the (−) AAP enantiomers. The anticonvulsant activity of the compounds is far more pronounced in the MES test with hardly any activity in the scMet test, in both mice and rats, by the i.p. and oral routes of administration, respectively, and protective indices greater than 50 are obtained by oral administration in the rat The potent activity of the (+) AAP enantiomers in the MES test is of great significance, because drugs used in the treatment of the two major types of seizures (partial and generalized) are quite distinct in their clinical effects. They also fall into two pharmacological classes, even though seizures may be induced experimentally by a wide variety of methods. The clinical aspects of certain generalized seizures, especially absence seizures, are highly correlated with experimental seizures produced in the scMet model. Likewise, partial seizures in humans correlate positively with experimental seizures elicited by the MES test (Porter, R. J. and Pitlick, W. H., In "Basic and Clinical Pharmacology", 4th Ed., B. G. Katzung Ed., Appleton & Lange, C.A., 1989, pp. 287–303).

The anticonvulsant compounds of the present invention may be administered to animals or humans at doses ranging from about 10 mg/kg up to about 200 mg/kg. Preferred levels of administration range from about 10 mg/kg up to 100 mg/kg. The active ingredients or compounds of this invention may be administered in any desired form by injection or in the oral form. Conventional adjuvents and carriers may be employed in combination with about 0.001 to 2.0 wt. % of the active ingredient. Thus, the anticonvulsant compositions of this invention may be administered in pill form or by injection. As indicated above, the dosage rate ranges from about 10 mg/kg up to about 200 mg/kg.

Screening Methodology to Determine Anticonvulsant Activity

In mice, i.p.: All compounds are emulsified in 0.5% methylcellulose. The solvent has been tested for anticonvulsant and toxic effects and found to introduce no significant bias into the testing of anticonvulsant activity. The compounds are administered intraperitoneally in a volume of 0.01 ml/gm to male Carworth Farms #1 mice weighing about 20 gm. All compounds are tested at least at three dose levels (30, 100 and 300 mg/kg) at 30 minutes and 4 hours after their administration.

The Maximal Electroshock Seizure Test (MES): Maximal electroshock seizures are elicited with a 60 Hz alternating current of 50 mA intensity in mice and about 150 mA intensity in rats (5–7 times that necessary to elicit minimal electroshock seizures), delivered for 0.2 sec via corneal electrodes. A drop of 0.9% saline is instilled in the eye prior to application of the electrodes in order to prevent the death of the animal. Abolition of the hind limb tonic extension component of the seizure is defined as protection and results are expressed as number of animals protected/number of animals tested. The Subcutaneous Pentylenetetrazol (Metrazole) Seizure Threshold Test (scMet): A 0.5% solution of 85 mg/kg of pentylenetetrazol is administered subcutaneously in the posterior midline 30 minutes or 4 hours after drug administration to the animal. Failure to observe even a threshold seizure (a single episode of clonic spasms of at least 5 sec duration) is defined as protection and the results are expressed as number of animals protected/number of animals tested.

Neurotoxicity is evaluated in mice by the rotorod ataxia test. The animal is placed on a wooden rod of 1 and ⅛ diameter rotating at 6 rpm. Normal mice can remain on a rod rotating at this speed indefinitely. Neurologic toxicity is defined as the failure of the animal to remain on the rod for 1 minute and is expressed as number of animals exhibiting toxicity/number of animals tested.

Anticonvulsant Quantification in Mice i.p.: The $ED_{50}$ values are determined in the MES, scMet and rotorod ataxia test. To determine the $ED_{50}$ values, five logarithmically spaced doses of the test compound are administered to animals (male Carworth Farms #1 mice) in groups of eight, to cover 0–100% protection, and the dose required to protect 50% of the animals ($ED_{50}$) together with its 95% confidence limits, is determined graphically.

Anticonvulsant Quantification in Rats p.o.: Substances which exhibit unusual potential as possible antiepileptic drugs, as determined from all prior testing will be subjected to anticonvulsant activity test in the rat (Sprague-Dawley strain). This species will be the subject of the complete anticonvulsant quantification test evaluation as described above, but after oral (gavage) administration of the candidate compound. These results will permit the critical comparison of the anticonvulsant activity and neurotoxicity of the agent under study with similar data previously obtained in mice. Substances which exhibit potential antiepileptic activity will be advanced for toxicity and selected pharmacology studies.

Neurological deficit in rats is examined by the positional sense test and gait and stance test. In the positional sense test, one hind leg is gently lowered over the edge of a table, whereupon the animal will quickly lift it back to normal position. Inability to do so rapidly indicates a neurologic deficit. In the gait and stance test, a neurologic deficit is indicated by a circular or a zigzag gait, ataxia, abnormal spread of the legs, abnormal body posture, tremor, hyperactivity, lack of exploratory behavior, somnolence, stupor, or catalepsy.

(+) AAP Enantiomers Derived from Optical Resolution of Racemic AAPs as Inhibitors of EAA Neurotransmission

EXAMPLE 4

EAAs are known to play important roles in excitatory neurotransmission in partial seizures as discussed earlier. In general, antiepileptic drugs effective against MES seizures alter ionic transport across excitable membranes [Porter, R. J., and Pitlick, W. H., In "Basic and Clinical Pharmacology", 4th Edn., B. G. Katzung, Ed., Appleton and Lange, CA 1989, pp. 287–303]. Based on this rationale, the (+) AAP enantiomers of this invention which are highly effective in the MES test, can be expected to be effective antagonists of NMDA-receptor mediated EAA neurotransmission and thus can be used to advantage in epilepsy, particularly complex partial seizures, stroke and Parkinson's disease where EAAs play a key role, and where there is a definite need for more effective drugs.

TABLE 3

Anticonvusant Testing of (+) Enantiomer (Compound 1 in Table 1) in the Hippocampal Kindled Rats

| | TIME COURSE | |
| --- | --- | --- |
| Time (min) | Seizure Score ± S.E.M. | Afterdischarge Duration (sec) ± S.E.M. |
| | Dose: 25 mg/kg | |
| Control | 4.88 ± 0.13 | 75.75 ± 6.62 |
| 15 | 4.63 ± 0.18 | 76.63 ± 7.34 |
| 45 | 3.75 ± 0.65 | 54.63 ± 12.54 |
| 75 | 4.13 ± 0.48 | 62.75 ± 10.46 |
| 105 | 5.00 ± 0.00 | 74.75 ± 6.44 |
| 135 | 4.50 ± 0.19 | — |
| | Dose: 50 mg/kg | |
| Control | 4.88 ± 0.13 | 72.86 ± 8.81 |
| 15 | 3.75 ± 0.53 | 56.43 ± 7.60 |
| 45 | 4.13 ± 0.40 | 63.38 ± 10.75 |
| 75 | 4.71 ± 0.18 | 63.14 ± 6.38 |
| 105 | 4.71 ± 0.18 | 74.57 ± 11.58 |
| 135 | 4.00 ± 0.69 | 61.43 ± 12.97 |
| 165 | 4.57 ± 0.20 | 73.14 ± 9.41 |
| | Dose: 75 mg/kg | |
| Control | 4.71 ± 0.18 | 75.14 ± 6.25 |
| 15 | 2.86 ± 0.59* | 63.29 ± 6.70 |
| 45 | 2.43 ± 0.69* | 55.43 ± 10.39 |
| 75 | 2.86 ± 0.59* | 74.57 ± 10.36 |
| 105 | 3.86 ± 0.34* | 68.57 ± 5.52 |
| 135 | 4.14 ± 0.26 | 65.00 ± 4.12 |
| | Dose: 100 mg/kg | |
| Control | 4.57 ± 0.20 | 74.71 ± 6.20 |
| 15 | 2.00 ± 0.69* | 63.43 ± 11.37 |
| 45 | 2.00 ± 0.58* | 63.29 ± 4.76 |
| 75 | 2.29 ± 0.61* | 75.43 ± 9.70 |
| 105 | 2.29 ± 0.71* | 71.00 ± 5.35 |
| | DOSE RESPONSES Time of Test: 45 min. | |

| Dose (mg/kg) | # Protected/ # Tested | Seizure Score ± S.E.M. | Afterdischarge Duration (sec) ± S.E.M. |
| --- | --- | --- | --- |
| 25 | 2/8 | 3.75 ± 0.65 | 54.63 ± 12.54 |
| 50 | 2/8 | 4.13 ± 0.40 | 63.38 ± 10.75 |
| 75 | 5/7 | 2.43 ± 0.69* | 55.43 ± 10.39 |
| 100 | 6/7 a | 2.00 ± 0.58* | 63.29 ± 4.76 |

*Significantly different from control.
a 2/7 toxic
ED50: 54.92 mg/kg
95% C.I. 23.13–94.98
Slope 2.93 ± 1.16

TABLE 4

Anticonvulsant Testing of (−) Enantiomer (Compound 2 in Table 1) in the Hippocampal Kindled Rats

| | TIME COURSE | |
| --- | --- | --- |
| Time (min) | Seizure Score ± S.E.M. | Afterdischarge Duration (sec) ± S.E.M. |
| | Dose: 100 mg/kg | |
| Control | 4.75 ± 0.16 | 74.25 ± 4.90 |
| 15 | 4.63 ± 0.38 | 69.88 ± 8.29 |
| 45 | 4.25 ± 0.49 | 74.88 ± 10.31 |
| 75 | 4.75 ± 0.16 | 82.50 ± 6.11 |
| 105 | 4.50 ± 0.50 | 75.75 ± 11.71 |

TABLE 4-continued

Anticonvusant Testing of (−) Enantiomer (Compound 2 in Table 1) in the Hippocampal Kindled Rats

| 135 | 4.75 ± 0.16 | 82.63 ± 5.04 |
| 165 | 4.13 ± 0.61 | 79.00 ± 12.92 |
| 195 | 3.88 ± 0.67 | 69.25 ± 11.15 |
| 225 | 4.25 ± 0.16 | 83.75 ± 5.17 |
| 255 | 4.00 ± 0.50 | 73.13 ± 11.97 |
| 285 | 4.83 ± 0.17 | 84.50 ± 6.76 |

DOSE RESPONSES
Time of Test: 195 min.

| Dose (mg/kg) | # Protected/ # Tested | Seizure Score ± S.E.M. | Afterdischarge Duration (sec) ± S.E.M. |
|---|---|---|---|
| 100 | 2/8 | 3.88 ± 0.67 | 69.25 ± 11.15 |

EXAMPLE 5

As discussed earlier, the (+) AAP enantiomers of this invention are highly effective in the MES test, and hence, may be expected to be effective in the kindling model as well, where too EAAs play an important role. The (+) AAP enantiomer, compound 1 in Table 1, was tested in the hippocampal kindled rat, by the i.p. route. The enantiomer significantly reduced seizure score and afterdischarge duration and the effect was dose-dependent. The results are illustrated in Table 3.

EXAMPLE 6

The (−) AAP enantiomer, compound 2 in Table 1, was also tested in the hippocampal kindled rat, by the i.p. route. The enantiomer had only moderate activity and the results suggested its ability to prevent/modify fully kindled seizures as shown in Table 4.

The Timed Intravenous Metrazol Seizure Threshold Test in Mice. i.p.

A compound that is active in the MES test and prevents seizure spread, can lower seizure threshold at the same time. Such a compound would have proconvulsant activity while at the same time prevent generalized tonic seizures. Mexiletine, a cardiac antiarrhythmic durg, is potent in the MES test, yet it lowers seizure threshold at doses slightly above the MES $ED_{50}$ in mice. The timed intravenous pentylenetetrazol (Metrazol) seizure threshold test in mice identifies those MES compounds with proconvulsant potential.

EXAMPLE 7

Mice were given the (+) and (−) enantiomers, compounds 1 and 2 in Table 1, intraperitoneally at the $ED_{50}$ and $TD_{50}$. At the time of maximal MES activity, an intravenous infusion of 0.5% heparinized solution of pentylenetetrazol (PT2) (0.34 ml/min) was started. The time to the appearance of the first myoclonic jerk (twitch) and the subsequent sustained clonic seizure (clonus) were the measured endpoints. Results were obtained for groups of ten treated and ten saline control mice and converted to the dose in mg/kg of PTZ necessary to produce the two endpoints. Proconvulsants lower the dose of PTZ required to produce the endpoint Anticonvulsant drugs such as valproic acid, ethosuximide an phenobarbital increase the amounts of PTZ required to produce the above endpoints.

Experiments were performed using three doses of 0, 36 and 149 mg/kg on each of 10 animals per dosage group. The time to "twitch" and the time to "clonus", the two components of the seizure elicited by the infusion of metrazol, were observed.

The amount of PTZ required to produce the twitch and clonus as well as the time to twitch and the time to clonus were both significantly raised in the case of the (+) enantiomer compound 1 but only in modest amounts in the case of compound 2.

Compound 1, the (+) enantiomer raised the PTZ dose from 31.23 mg/kg in the control group to 33.31 mg/kg in the 149 mg/kg dosage group for the twitch component, and 37.60 mg/kg in the control group to 46.84 mg/kg in the 36 mg/kg dosage group and to 74.13 mg/kg in the 149 mg/kg dosage group for the clonus component. Simultaneous with this increase, the time to twitch was raised from 33.03 seconds in the control group to 34.91 seconds in the 36 mg/kg dosage group and 35.01 seconds in the 149 mg/kg dosage group. Likewise, the time to clonus was raised from 39.71 seconds in the control group to 48.56 seconds in the 36 mg/kg dosage group and 77.56 seconds in the 149 mg/kg dosage group.

The Therapeutic Potential of (+) AAP Enantiomers, as Clinically Useful Antiepileptic Drugs in the Treatment of Partial Seizures: Potent Orally Active, Nonneurotoxic Anticonvulsant Agents, Effective in the Kindling Model of Epilepsy The (+) AAP enantiomers of this invention are far superior to the (−) AAP enantiomers as well as the racemic compounds, as seen from Table 2, Table 3 and Table 4.

This invention relating to (+) AAP enantiomers has been described herein with reference to certain preferred embodiments. However, as obvious variations thereon will become apparent to those skilled in the art, the invention is not to be considered as limited thereto.

I claim:

1. An aminoalkylpyridine compound of the following formula:

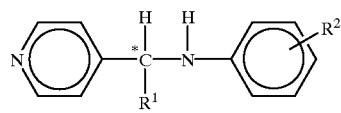

wherein $R^1$ is ethyl and $R^2$ is 3,4-dichloro, p- or m-chloro or p-bromo.

2. An orally effective, non-neurotoxic anticonvulsant composition comprising as the active ingredient an anticonvulsive effective amount of an (+) aminoalkylpyridine enantiomer compound of the formula:

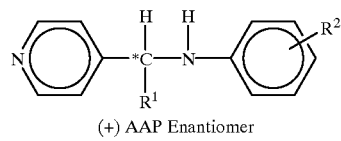

(+) AAP Enantiomer wherein $R^1$ is ethyl and $R^2$ is 3,4-dichloro, p- or m-chloro or p-bromo and a pharmaceutical carrier.

3. An orally effective, non-neurotoxic anticonvulsant composition comprising as the active ingredient, an anticonvulsive effective amount of an (−) aminoalkylpyridine enantiomer compound of the formula:

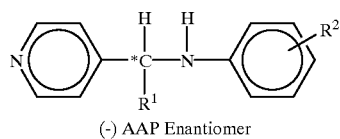

(-) AAP Enantiomer wherein R$^1$ is ethyl and R$^2$ is 3,4-dichloro, p- or m-chloro or p-bromo and a pharmaceutical carrier.

4. A (+) aminoalkylpyridine enantiomer compound of the following formulae:

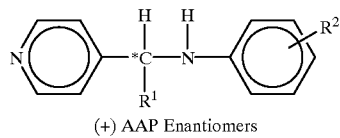

(+) AAP Enantiomers wherein R$^1$ is methyl or ethyl and R$^2$ is 3,4-dichloro, p- or m-chloro, or p-bromo.

5. A (+) aminoalkylpyridine enantiomer compound according to claim 4 wherein R$^1$ is methyl and R$^2$ is p-chloro.

6. A (+) aminoalkylpyridine enantiomer compound according to claim 4 wherein R$^1$ is methyl and R$^2$ is m-chloro.

7. A (+) aminoalkylpyridine enantiomer compound according to claim 4 wherein R$^1$ is methyl and R$^2$ is 3,4-dichloro.

8. A (+) aminoalkylpyridine enantiomer compound according to claim 1 wherein R$^1$ is ethyl and R$^2$ is p-chloro.

9. A (+) aminoalkylpyridine enantiomer compound according to claim 1 wherein R$^1$ is ethyl and R$^2$ is 3,4-dichloro.

10. A (+) aminoalkylpyridine enantiomer compound according to claim 4 wherein R$^1$ is methyl and R$^2$ is p-bromo.

11. A (−) aminoalkylpyridine enantiomer compound according to claim 1 wherein R$^1$ is ethyl and R$^2$ is p-chloro.

12. A (−) aminoalkylpyridine enantiomer compound according to claim 1 wherein R$^1$ is ethyl and R$^2$ is 3,4-dichloro.

13. A potent orally effective, non-neurotoxic anticonvulsive composition comprising as the active ingredient, an anticonvulsive effective amount of a (+) aminoalkylpyridine enantiomer compound having the formulae:

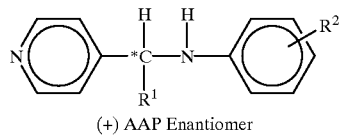

(+) AAP Enantiomer wherein R$^1$ is methyl or ethyl and R$^2$ is 3,4-dichloro, p- or m-chloro or p-bromo and a pharmaceutical carrier.

14. A composition according to claim 13 wherein R$^1$ is methyl and R$^2$ is p-chloro.

15. A composition according to claim 13 wherein R$^1$ is methyl and R$^2$ is m-chloro.

16. A composition according to claim 13 wherein R$^1$ is methyl and R$^2$ is 3,4-dichloro.

17. A composition according to claim 2 wherein R$^1$ is ethyl and R$^2$ is p-chloro.

18. A composition according to claim 2 wherein R$^1$ is ethyl and R$^2$ is 3,4-dichloro.

19. A composition according to claim 13 wherein R$^1$ is methyl and R$^2$ is p-bromo.

20. A composition according to claim 3 wherein R$^1$ is ethyl and R$^2$ is p-chloro.

21. A composition according to claim 3 wherein R$^1$ is ethyl and R$^2$ is 3,4-dichloro.

22. A potent orally effective, non-neurotoxic anticonvulsant composition, highly effective in the MES test and also in the hippocampal kindled rat and useful for the treatment of partial seizures and comprising as the active ingredient, an anticonvulsive effective amount of a (+) aminoalkylpyridine enantiomer compound of the formulae,

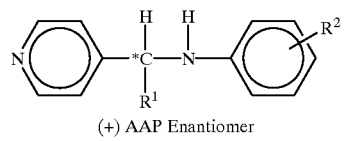

(+) AAP Enantiomer wherein R$^1$ is methyl and R$^2$ is p-chloro and a pharmaceutical carrier.

23. A potent orally effective, non-neurotoxic anticonvulsant composition, highly effective in the MES and hippocampal kindled rat tests and which raises the seizure threshold upon infusion of Metrazol and comprising as the active ingredient, an anticonvulsive effective amount of a (+) aminoalkylpyridine enantiomer compound of the formulae,

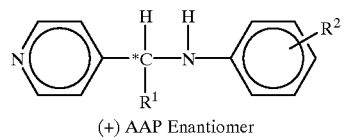

(+) AAP Enantiomer wherein R$^1$ is methyl and R$^2$ is p-chloro and a pharmaceutical carrier.

24. A composition according to claim 13, wherein a sufficient amount of the effective (+) or aminoalkylpyridine enantiomer ingredient is contained in said composition to provide a dosage amount ranging from about 10 mg/kg to 200 mg/kg.

25. A substantially pure (+) aminoalkylpyridine enantiomer compound according to claim 4.

26. A method for the treatment of convulsive disorders in mammals which comprises administration thereto of an effective dosage amount of an anticonvulsant composition of claim 13.

27. A method according to claim 26 wherein the composition is administered in a dosage amount ranging from about 10 mg/kg to 200 mg/kg of body weight.

28. A method of separating an (+) enantiomer from a racemic mixture of compounds according to claim 3 having the following formula:

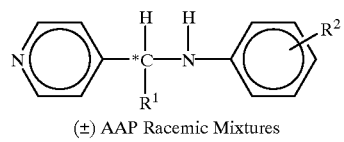

(±) AAP Racemic Mixtures the method comprising:

treating the (±) AAP racemic mixture with dibenzoyl tartaric acid to separate the (+) AAP enantiomer from the (±) AAP racemic mixture.

29. The method of claim 28, wherein the (+) AAP enantiomer is separated with high optical purity.

30. A method for the optical resolution of a racemic mixture of aminoallylpyridine according to claim 28 wherein $R^1$ is methyl and $R^2$ is p-chloro.

31. A method for the optical resolution of a racemic mixture of aminoalkylpyridine according to claim 28 wherein $R^1$ is methyl and $R^2$ is m-chloro.

32. A method for the optical resolution of a racemic mixture of aminoalkylpyridine according to claim 28 wherein $R^1$ is methyl and $R^2$ is 3,4-dichloro.

33. A method for the optical resolution of a racemic mature of aminoalkylpyridine according to claim 28 wherein $R^1$ is ethyl and $R^2$ is p-chloro.

34. A method for the optical resolution of a racemic mixture of aminoalkylpyridine according to claim 28 wherein $R^1$ is ethyl and $R^2$ is 3,4-dichloro.

35. A method for the optical resolution of a racemic mixture of aminoalkylpyridine according to claim 28 wherein $R^1$ is methyl and $R^2$ is p-bromo.

* * * * *